(12) United States Patent
Cuypers et al.

(10) Patent No.: US 7,867,180 B2
(45) Date of Patent: Jan. 11, 2011

(54) IMMOBILISATION DEVICE

(75) Inventors: Steven Cuypers, Gravenwezel (BE); Bogdan Bogdanov, Borgerhout (BE)

(73) Assignee: Orfit Industries, Wijnegem (BE)

( * ) Notice: Subject to any disclaimer, the term of this patent is extended or adjusted under 35 U.S.C. 154(b) by 0 days.

(21) Appl. No.: 11/797,500

(22) Filed: May 3, 2007

(65) Prior Publication Data

US 2007/0272256 A1   Nov. 29, 2007

(30) Foreign Application Priority Data

May 8, 2006   (EP) ................... 06113620

(51) Int. Cl.
  *A61F 5/00*   (2006.01)
  *B32B 3/00*   (2006.01)
(52) U.S. Cl. ...................... 602/8; 428/316.6
(58) Field of Classification Search ............ 602/8, 602/6, 5, 1; 525/194, 192, 195, 197, 198, 525/211, 240; 156/78; 428/316.6
  See application file for complete search history.

(56) References Cited

U.S. PATENT DOCUMENTS

| 3,414,533 | A | * | 12/1968 | Unterstenhoefer et al. .... 524/62 |
| 4,273,115 | A | * | 6/1981 | Holland et al. ................ 602/7 |
| 4,286,586 | A | * | 9/1981 | Potts ............................ 602/7 |
| 4,309,990 | A | * | 1/1982 | Brooks et al. .................. 602/8 |
| RE32,028 | E | * | 11/1985 | Fischer ....................... 525/194 |
| 5,807,291 | A | * | 9/1998 | Larson et al. .................. 602/8 |
| 2008/0154164 | A1 | * | 6/2008 | Sheehan et al. ................ 602/7 |

FOREIGN PATENT DOCUMENTS

JP   2005008891   *   1/2005

OTHER PUBLICATIONS

Translation of JP-2005008891 A.*

* cited by examiner

*Primary Examiner*—Patricia M Bianco
*Assistant Examiner*—Tarla R Patel
(74) *Attorney, Agent, or Firm*—Dykema Gossett PLLC

(57) ABSTRACT

The present invention relates to a transparent immobilization device which is able to be molded direct on a patient and which is provided to cover at least a part of a patients' body that needs to be fixed, supported and/or immobilized, which immobilization device is at least partly made of a plastic material. The immobilization device is at least partly made of a sheet of a material comprising at least one thermoplastic elastomer which is a copolymer of ethylene with at least one α-olefin having 3-10 carbon atoms, or a blend of two or more of such copolymers. The present invention also relates to a method for producing such an immobilization device, according to which the plastic material is first heated to a temperature which is 15-20° C. above the melting temperature, then cooled to a temperature which may be supported by the body and molded on the body part of the patient that needs to be immobilized.

15 Claims, No Drawings

IMMOBILISATION DEVICE

BACKGROUND OF THE INVENTION

1. Field of the Invention

The present invention relates to a transparent immobilization device which is provided to cover at least a part of a patient's body that needs to be fixed, supported and/or immobilized, wherein the immobilization device is at least partly made of a plastic material.

2. The Prior Art

Immobilization devices are frequently used in radiation therapy and diagnostic imaging for the purpose of immobilizing a body part in a fixed and reproducible position with respect to an irradiation source, in orthopedic applications for the purpose of immobilizing inflamed or injured joints in case of trauma or diseases, for supporting and immobilizing ligaments and muscular structures, in physical rehabilitation applications and in podiatry for example as insole (foot-bed) applications. A wide variety of plastic materials have been used in the art for making in orthopedic or other fixation or immobilization devices. However, only a limited number of plastic materials have a melting temperature which is sufficiently low to permit direct molding to the patients' body without causing burn injuries. Amongst those plastic materials, only a limited number have a sufficient formability and elasticity in the molten state at a temperature which can be supported by the body, to permit direct molding on a patients' body. Direct molding to the patients' body is important, as it permits adapting the size and shape of the immobilization device directly to each individual patient, in the position in which the body part is to be immobilized. Examples of plastic materials suitable for direct molding to a body part include thermoplastic materials for example polyurethane, transpolyisoprene, polyesters for example polycaprolactone or blends of two or more of these materials.

However, the hitherto used materials are opaque, they are non-transparent. As a consequence, they do not permit observing the skin covered by it, nor do they permit adjusting the positioning of the material using markers present on one or both of the immobilization device and the body part to be covered by the plastic material. This is a serious disadvantage in applications such as radiation therapy and diagnostic imaging, where it is of utmost importance that with intermittent treatments, a highly reproducible re-positioning and fixation of the immobilization device is provided and that a reproducible positioning, fixation and immobilization of the body part in a desired position may be guaranteed. Besides being opaque, the known plastic materials are quite rigid and hard which goes at the expense of the wearing comfort and they show significant shrinking upon crystallization when cooling down from the melting temperature. As the immobilization device in the course of the molding is usually is formed in such a way that it fits as close as possible to the body part to be immobilized, there is a risk that it fits too tightly after cooling and crystallization and feels uncomfortable to the patient.

A vast number of the industrially available engineering plastic materials have a melting temperature which is above 100° C. These materials may be suitable for use in immobilization structures as well, provided they are molded using a positive mold which is made to correspond as close as possible to the body part to be immobilized. This thus involves the additional step of producing a positive mold which must correspond as closely as possible to the body part to be immobilized.

It is therefore the object of the present invention to provide a transparent immobilization device which may be directly molded onto the body part that needs to be immobilized to fit to it as closely as possible, but which still leaves the possibility of moving the body part within pre-determined limits.

SUMMARY OF THE INVENTION

The immobilization device of this invention is at least partly made of a plastic material which includes at least one thermoplastic elastomer, in particular a copolymer of ethylene with at least one α-olefin having 3-10 carbon atoms, or a blend of two or more of such copolymers.

Preferred plastic material include those comprising an amount of a thermoplastic elastomer which is a copolymer of ethylene with one or more α-olefins having 3-10 carbon atoms, more preferably a copolymer of ethylene with 1-butene or a copolymer of ethylene with 1-octene or a blend of two or more of these copolymers.

The inventors have found that these plastic materials are transparent and mouldable at low temperature direct on a patient. This is renders the immobilization device of this invention particularly suitable for use in radiation therapy and diagnostic imaging and in all other applications where an accurate re-positioning of the immobilization device in intermittent treatments is of utmost importance. The transparency permits using positioning markers on one or both of the immobilization device and the body part to facilitate re-positioning.

Besides that, once molded, the immobilization device of this invention has been found to provide improved comfort to the patient because it feels soft to the skin, it has a higher flexibility and reduced rigidity even after complete crystallization as compared to the immobilization devices known hitherto. As a consequence of the reduced rigidity, the material may be easily cut with good and smooth finishing edges using conventional tools such as scissors and knives.

The relatively low bending modulus of the ethylene copolymer material permits designing the immobilization device such that the local pressure exerted by the immobilization device to the body part covered by it is reduced, such that the body part is immobilized in a desired configuration whereby some moveability, to a limited extent is still permitted to provide functional mobility of the immobilized body part. By permitting functional mobility, the risk that the immobilization device is sensed excessively rigid and stiff by the patient is minimized. This functional mobility and reduced local pressure is becoming an important feature in specific applications.

The inventors have also found that the immobilization device of this invention shows limited shrinking when cooling down from the molten or activated state. The degree of shrinking has been found significantly smaller than that observed with other materials known from the art. This is particularly advantageous as it permits minimizing the risk to a too tight fitting and the ensuing need to re-molding of the device, as well as the risk to sensing of excessive pressure or compression to the immobilized body part. This is an advantage over known prior art materials which usually show significant shrinking during crystallization while cooling.

It is remarked that the person skilled in the art would not consider using the above-described plastic materials in the production of immobilization devices that are directly molded onto the patient. Although the claimed materials have a melting temperature which is usually below about 70° C., mostly maximum about 60° C., the material shows a high toughness when heated to the melting temperature and when cooled at room temperature, it is then hardly mouldable. When analyzing this problem, the inventors observed that this problem could be solved by heating the plastic material to a temperature which is 15-20° C. above the melting temperature, for example about 75-90° C. At these temperatures the material is completely molten, soft and looses its crystalline memory and becomes mouldable. The inventors have also observed that the mouldability of the material is maintained upon cooling to a temperature which may be supported by the body, for example about 55-60° C., for a longer period of time than would normally be expected. They have explained this by the surprising finding that the crystallization rate of this material is significantly slower than the cooling rate when cooling from 75-90° C. at room temperature. As a consequence, mouldability of the material is preserved for a longer period of time before it starts to crystallize and harden than could be expected.

For those applications requiring quite extreme stretching of the material to provide good fit and sufficient immobilization of the body part to be immobilized, the melt strength may be improved by using copolymers that are at least partly cross-linked. The degree of cross-linking may be higher or lower depending on the envisaged melt strength. High melt strength is particularly important for immobilization devices or masks used in radiation therapy and similar applications, where strong fixation and reproducible positioning and comfort of the patient are a prerequisite imposed by the nature of the application. Cross-linking may be achieved with any technique considered suitable by the person skilled in the art, for example using chemical cross-linking for example using peroxides as a cross-linking agent (for example dicumyl peroxide) or high energy irradiation.

Wearing comfort to the patient and soft surface feeling may be improved by using a plastic material which is at least partially expanded. Although full transparency will mostly be lost by the presence of foam cells, the material remains flexible and sufficiently thermo formable.

An immobilization device with an improved mechanical strength is obtained with a plastic material which contains an amount of a reinforcing material. The nature of the reinforcing material is not critical to the invention and may be adapted by the person skilled in the art taking into account the envisaged use of the immobilization device. The reinforcing material may for example be chosen from the group of at least one fibrous reinforcing material, particles of foamed glass, glass bubbles, hollow glass spheres, glass powder or foamed minerals. Glass powder is preferred as it presents the advantage that when incorporated into the ethylene copolymer plastic material, the transparency of the plastic material is maintained to a large degree. The at least one fibrous reinforcing material may be selected from the group of loose glass fibers, fibers of a plastic material, carbon fibers, natural fibers such as cotton or flax or mixtures containing two or more of these types of fibers, although most of these will preferably not be used in those applications when the occurrence of some transparency or translucency are key parameters. Minimum loss of transparency is obtained with glass bubbles having a diameter more than 100 μm. An optimum compromise between strength and translucency is obtained when the reinforcing material is present in an amount of between 5 and 20 wt. % with respect to the total weight of the plastic material.

Preferred copolymers of ethylene and 1-butene and/or 1-octene have a melting point which is between 45° C. and 70° C., preferably between 45° C. and 60° C. This melting point is measured from a peak observed in a DSC heating curve, at a heating rate of 10°/minute. Because of the low melting point, direct molding to the patients' body part that needs to be immobilized may be done, while activation or melting of the material can be easily performed in an oven or a hot water bath. Despite the relatively high crystallization temperature (44-50° C.) shown by these materials which may be advantageous in numerous applications, the inventors have observed that it takes some time before crystallization starts and is completed and that the induction time of crystallization is still long enough to permit good shaping and molding.

It is preferred that the copolymer of ethylene and 1-butene and/or ethylene and 1-octene has a melt index which is between 50 and 0.1 g/10 min, preferably between 30 and 0.5 g/10 min. With melt index is meant the melt index measured according to ASTM D1238 test method at 190° C., 2.16 kg. These materials are preferred as their viscosity in the melt is not too high, nor too low to permit processing by injection moulding, compression moulding or extrusion and to use this material for direct molding.

The preferred ethylene copolymer has some, but limited crystallinity. The total crystallinity of the ethylene copolymer is preferably less than 25%, more preferably less than 21%. Herein % of crystallinity is expressed as wt. % of crystalline part of plastic material with respect to the total weight of plastic material.

Preferred copolymers of ethylene and 1-butene or ethylene and 1-octene have ultimate tensile strength of at least 2 MPa, but less than 20 MPa as such materials may be molded to fit snuggly around the limbs to attain the desired compression of soft tissues, which is important in particular for fracture braces and knee cages as well as for the healing of burn wounds and the scars associated therewith. Materials having such tensile strength have been found to show a minimum risk of tearing apart of the material in normal circumstances of manual molding. These copolymers show improved moldability and may be molded in such a way that they fit more closely to the anatomic shape of the body part to be immobilized than could be achieved up to now, without loosing comfort. Preferred copolymers of ethylene and 1-octene and ethylene and 1-butene have a ultimate tensile strength which is between 2 and 15 MPa. With tensile strength is meant the tensile strength measured according to ASTM method 683.

Preferred copolymers of ethylene and 1-octene and ethylene and 1-butene have a flexural modulus which is sufficiently high but not too high, to provide functional mobility of the immobilization device. Thereto, the flexural modulus is preferably at least 7 but less than 35 MPa as determined with ASTM method D790.

If it is desirable to adapt one or more of the melt strength, tensile strength, flexural modulus of the immobilization device, the plastic material may contain between 5 and 40 wt. % with respect to the weight of the plastic material of at least one second plastic material. Above 40-45 wt. % there is a risk that either the melting temperature or one or more of the mechanical properties change too much. Preferred second plastic materials are selected from the group of thermoplastic elastomers, polyurethane, polyisoprene, polyester in particular polycaprolactone, polyolefins, in particular polyethylene, polypropylene or ethylene-propylene copolymers; poly-ethylenevinylacetate; polyvinylchloride; polystyrene; polyacrylate or polymethacrylate or blends of two or more of these materials.

The immobilization device of the present invention is suitable for use in a wide variety of applications, for example as a fixation device in radiation therapy and diagnostic imaging, in orthopedic applications, in podiatry for example as insole (foot-bed) applications.

The immobilization device of the present invention presents the advantage of combining several properties which are highly desired in the technical field at state.

The immobilization device of this invention presents the advantage that it is directly moldable on the human body and that it is transparent, which renders it suitable for use in applications for which hitherto no adequate materials were available. Due to the transparency, it is possible
- to observe whether or not the immobilization device has been properly molded to the body part and fits sufficiently tight, this being particularly relevant in the protection of fractures;
- to observe the anatomy of the underlying body part during molding as well as later on during use;
- to monitor the occurrence of potential pressure areas both during molding and later on during use and if needed the immobilization device may be re-molded to adapt or adjust the fixation force.

This is particularly important for example with circumferential hand splints, fracture bracing and compression pads, test sockets or orthopedic shoe wear. The transparency of the immobilization device is also important when the device is used with body parts having a sensible skin where it is of importance that the condition of the skin may be observed in the course of the treatment, and in case the immobilization device is used in pressure therapy in the healing of burn wounds as it permits controlling skin blanching. The fact that the plastic material is transparent also presents specific advantages in radiation oncology, radiotherapy and diagnostic imaging, where often the skin of the body part to be irradiated is marked to permit a reproducible positioning of the immobilization device especially with intermittent treatments and to permit an irradiation at reproducible locations on the body.

Because the immobilization device, besides being transparent also shows some flexibility, functional mobility of the immobilized part may be provided which reduces the risk to the occurrence of pressure points on the skin. Besides that pressure points on the skin may be observed as a function of time and the fixation force provided by the immobilization device may be adjusted to reduce pressure and to increase the comfort of the patient. The relatively high bending modulus and a high melt strength, result in an immobilization device which is rubber-like when the material is in the molten state, which material may be stretched and shaped to optimize fit to the body part, at low risk to tearing apart. The high tensile strength permits making thin sheets, thus improving wearing comfort.

The immobilization device of this invention is mouldable at room temperature and remains mouldable for a longer period of time than could be expected based on the materials' properties, which is transparent and permits observing the body part underneath, which shows a high melt strength in the molten state and permits optimum stretching and forming during moulding, which shows a bending modulus which is sufficiently high to limit but still permit some moving of the body part contained in it.

The inventors have also observed that the immobilization device of this invention shows a high elastic memory, in particular that it can be easily re-moulded after having been moulded for a first time. Re-moulding is done by re-heating the device to the melting temperature of the material, followed by moulding the material to the patient's body. The re-moulding permits producing consecutive immobilization devices from one and the same starting device, and to gradually change the degree and position of immobilization with time. The fact that the material is re-mouldable permits providing relief to positions where pressure is sensed by the patient after the immobilization device has been moulded for a first time to fit to the body part that needs immobilization, and it permits correcting or complete re-moulding the immobilization device in case it has been incorrectly moulded or in case the position of the immobilized part needs to be changed in the course of time. The possibility to re-moulding presents the advantage that the device is re-sizable and allows patient adaptation. This is important in case the immobilization device is available in a few sizes only, as it permits personalizing the device at an economically reasonable cost.

The inventors have further observed that the above described thermoplastic copolymers of ethylene and 1-butene and ethylene and 1-octene show a high impact resistance which results in an immobilization device with a good shock resistance, and a high tear strength even in the molten or partially cooled down state as a consequence of which there is a minimum risk to tearing apart of the material during manual moulding.

The inventors have further observed that the above described thermoplastic copolymers of ethylene and 1-butene and ethylene and 1-octene show excellent self-adhesion in a molten state but at the same time is non-sticky and does not stick to the skin of body part. This means that enclosing immobilization devices can be moulded of one and the same material, without necessitating the use of adhesives or the provision of additional closure parts, such as for example Velcro®. This simplifies production. On the other hand, the need of using release means such as talc or release film materials to be applied between the immobilization device and the skin, may be overcome. The ethylene copolymers used in the immobilization device of this invention further present the advantages of showing an excellent finish, to remain clear and clean for a long period of time, to be easy to clean and to show good water resistance. The latter allows them to be functionally used in a wide variety of circumstances, even in water. On the other hand, the material shows a minimum tendency to absorb perspiration. Because the material is translucent to X-rays, the healing of the body part in the course of time may be observed without the need of removing the immobilization device.

Within the scope of the present invention, the immobilization device may be partly made of the above described copolymer of ethylene with at least one α-olefin having 3-10 carbon atoms, or a blend of two or more of such copolymers or it may be wholly made thereof. In case the immobilization device is partly made of the above described copolymer, the remaining part can be made of any suitable plastic material known to the person skilled in the art.

The present invention also relates to a method for moulding the plastic material to the body part that needs to be immobilized. An immobilization device of the present invention is produced by cutting a sheet of a plastic material to the contours which correspond to the body part that is to be immobilized. As a plastic material use is made of a sheet having a thickness of 3 mm, which is a blend of 30 wt. % of a copolymer of ethylene and 1-butene with density of 0.8 g/cm$^3$ and a melt flow index of 30 g/10 min with 70 wt. % of a copolymer of ethylene and 1-butene with density of 0.8 g/ccm and different melt flow index of 1 g/10 min. The plastic material is heated to a temperature which is 15-20° C. above the melting temperature so that the material looses its crystalline memory, after which the material is cooled to a temperature which may be supported by the body. Then, the plastic material is moulded on the body part of the patient that needs to be immobilized. In particular example, the plastic material is heated to a temperature of about 75-90° C., after which it is allowed to cool to a temperature of about 55-60° C. For example a sheet made of a plastic material having a melting temperature of about 60° C., is heated in a hot water bath maintained at a temperature of 75° C. until it has reached that temperature. The sheet is removed from the water bath and allowed to cool to 60° C. Then the sheet is moulded to the hand of the patient.

The invention claimed is:

1. A transparent immobilization device which is able to be moulded direct on a patient and which is provided to cover at least a part of a patient's body that needs to be fixed, supported and/or immobilized, which immobilization device is at least partly made of a sheet of a material comprising at least one thermoplastic elastomer which is a copolymer of ethylene with at least one α-olefin having 4-10 carbon atoms and a crystallinity which is less than 25%, or a blend of two or more of such copolymers, and wherein the material contains between 1 and 45 wt. % with respect to the weight of the material of at least one second material.

2. The immobilization device as claimed in claim 1, wherein the material includes an amount of a thermoplastic elastomer which is a copolymer of ethylene and 1-butene or 1-octene or a blend of two or more of these copolymers.

3. The immobilization device as claimed in claim 1, wherein the material is at least partly cross-linked.

4. The immobilization device as claimed in claim 1, wherein the material is at least partly made of a material which is at least partly expanded.

5. The immobilization device as claimed in claim 1, wherein the material contains an amount of a reinforcing material.

6. The immobilization device as claimed in claim 5, wherein the reinforcing material use is made of a material chosen from the group of at least one fibrous reinforcing material, glass bubbles, glass spheres and glass powders.

7. The immobilization device as claimed in claim 6, wherein the at least one fibrous reinforcing material is selected from the group of loose glass fibers, carbon fibers or fibers of a plastic material.

8. The immobilization device as claimed in claim 6, wherein the glass bubbles have a diameter of between 50-200 μm.

9. The immobilization device as claimed in claim 8, wherein the reinforcing material is present in an amount of between 10 and 45 wt. % with respect to the total weight of the material.

10. The immobilization device as claimed in claim 1, wherein the copolymer has a melting point which is between 45 and 70° C.

11. The immobilization device as claimed in claim 1, wherein the copolymer has a melt index of below 30 g/10 min.

12. The immobilization device as claimed in claim 1, wherein the copolymer has a tensile strength of at least 2 MPA and flexural modulus of at least 7 MPa.

13. The immobilization device as claimed in claim 1, wherein the second material is selected from the group consisting of thermoplastic elastomers, polyurethane, trans-polyisoprene, polyester in particular polycaprolactone, polyolefins, in particular polyethylene, polypropylene or ethylene-propylene copolymers; poly-ethylvinylacetate; polyvinylchloride; polystyrene; polyacrylate and polymethacrylate or blends of two or more of these materials.

14. A method for producing an immobilization device as claimed in claim 1, wherein the material is heated to a temperature which is 15-20° C. above a melting temperature thereof, after which the material is cooled to a temperature which may be supported by the body, after which the material is moulded on the body part of the patient that needs to be immobilized.

15. The method as claimed in claim 14, wherein the material is heated to a temperature of about 75-90° C., after which it is allowed to cool to a temperature of about 55-60° C.

\* \* \* \* \*